United States Patent [19]

Animati et al.

[11] Patent Number: 5,801,152
[45] Date of Patent: Sep. 1, 1998

[54] ANTRACYCLINE DISACCHARIDES, PROCESS FOR THEIR PREPARATION, AND PHARMACEUTICAL COMPOSITIONS CONTAINING THEM

[75] Inventors: Fabio Animati, Rome; Paolo Lombardi, Cesate; Frederico Arcamone, Nerviano; Amalia Cipollone, Rome, all of Italy

[73] Assignees: A. Menarini Industrie Farmaceutiche Riunite S.r.L, Florence; Bristol-Myers Squibb S.p.A., Sermonta, both of Italy

[21] Appl. No.: 644,602

[22] Filed: Mar. 28, 1996

[30] Foreign Application Priority Data

Sep. 30, 1993 [IT] Italy .................... FI93A0187

[51] Int. Cl.⁶ .................... A61K 31/70; C07H 15/24; C07H 1/00
[52] U.S. Cl. .................... 514/34; 536/6.4; 536/18.5; 536/18.6
[58] Field of Search .................... 536/6.4, 18.5, 536/18.6; 514/34

[56] References Cited

U.S. PATENT DOCUMENTS 4,918,172  4/1990  Yoshimoto et al. .................... 536/6.4

FOREIGN PATENT DOCUMENTS 0457215  1/1996  European Pat. Off.
2751395  5/1978  Germany.
3641833  6/1988  Germany.

OTHER PUBLICATIONS

Abbaci et al., "Carbohydrate Research", 228, pp. 171–190 (1992).
Horton et al., "The Journal of Antibiotics", vol. 46, No. 11 pp. 1720–1730 (1993).
DeMesmaeker et al. "Tetrahedron Letters", vol. 30, No. 29, pp. 3773–3776 (1989).
Corey et al., "J. Org. Chem.", vol. 38, No. 18, pp. 3223–3224 (1973).
Horton et al., "The Journal of Antibiotics", vol. XXXVII, No. 8, pp. 853–858 (1984).
Smith et al., "J. Org. Chem.", vol. 42, No. 23, 3653–3660 (1977).
Del Nero et al., "Gazzetta Chimica Italiana", 114, 517–520 (1984).
Kimura et al., "Bull. Chem. Soc. Jpn.", 59, pp. 423–431 (1986).

P. Smid et al., "J. Carbohydrate Chemistry", 10(5), 833–849 (1991).
El Khadem et al., "Carbohydrate Research", 74, 199–205, (1979).
Kolar et al., "Carbohydrate Research", 208, 67–81 (1990).
Friesen et al., "Tetrahedron", vol. 1, No. 1, 103–112 (1990).
Boivin et al., "Tetrahedron", vol. 37, No. 24, pp. 4219–4228 (1981).

Primary Examiner—Elli Peselev
Attorney, Agent, or Firm—Abelman, Frayne & Schwab

[57] ABSTRACT

The present invention is referred to compounds of general formula (I) and (II), respectively

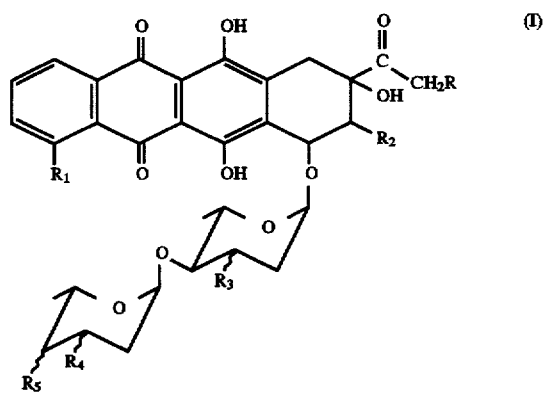

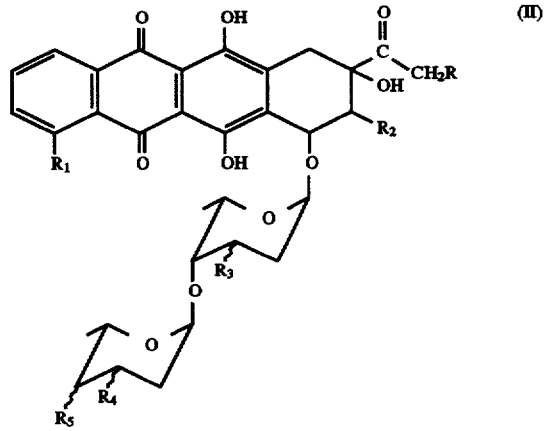

their pharmaceutically acceptable salts, the process for their preparation, and the pharmaceutical compositions containing them.

18 Claims, No Drawings

ANTRACYCLINE DISACCHARIDES, PROCESS FOR THEIR PREPARATION, AND PHARMACEUTICAL COMPOSITIONS CONTAINING THEM

This application is a continuation-in-part of International Application PCT/EP94/03201 having an international filing date of Sep. 26, 1994.

FIELD OF THE INVENTION

The present invention is referred to compounds of general formula (I) and (II), respectively

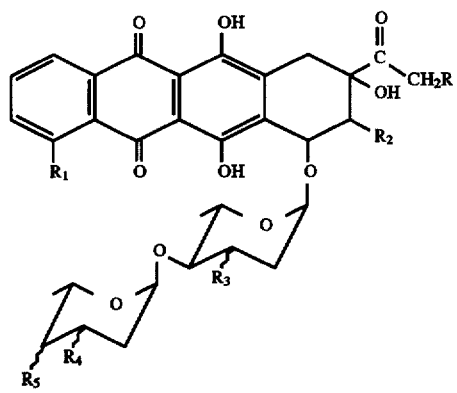

(I)

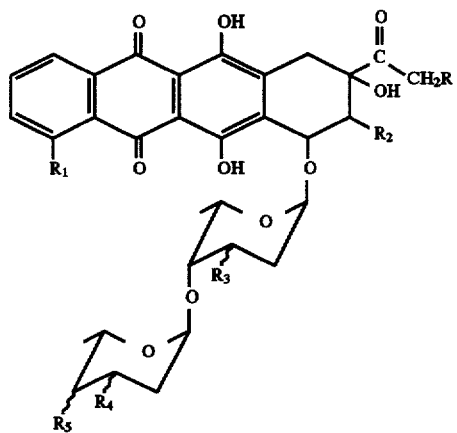

(II)

where:

R is H or OH or the $OR_7$ group where $R_7$=CHO or $COCH_3$ or the acylic residue of a carboxylic acid containing up to 6 carbon atoms;

$R_1$ is H or OH or $OCH_3$;

$R_2$ is H or F;

$R_3$ is H or OH;

$R_4$ and $R_5$, identical or different, are each H or OH or $NH_2$; and bond symbol ⸺ indicates that substituents $R_3$, $R_4$, and $R_5$ may be either in axial or equatorial position; and their pharmaceutically acceptable salts having anticancer properties.

As may be seen in the above formulas, compounds (I) and (II) differ exclusively in the space arrangement of the glycosidic groups and, therefore, may be represented by formula (A)

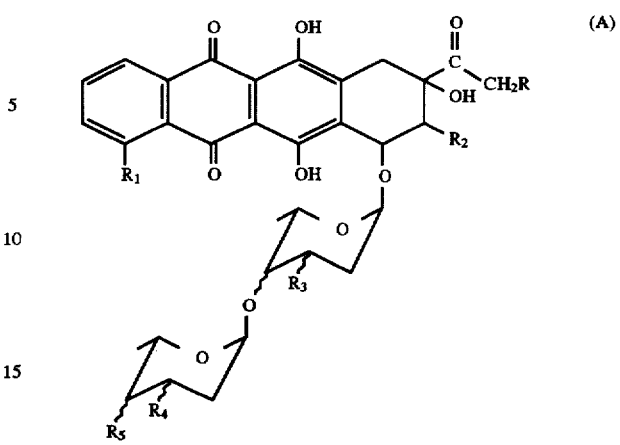

(A)

where symbol ⸺ indicates that the second carbohydrate residue may be bound to carbon atom 4' of the first sugar either in axial or in equatorial position.

The present invention is also referred to the process for the preparation of said compounds, their pharmaceutically acceptable salts, and the pharmaceutical compositions containing them.

STATE OF THE ART

Daunorubicin and doxorubicin are well-known antibiotics that are currently used in the clinical practice for the treatment of a variety of solid tumours and leukaemia (F. Arcamone in "Doxorubicin: Anticancer Antibiotics", A. C. Sartorelli, Ed., Academic Press, N.Y., 1981).

Compounds having a structure similar to those described in the present application but presenting only one glycosidic group are described in EP-457215, WO 80/00305 and WO 90/07519. Compounds showing two or more sugar moieties wherein the sugar directly linked to the aglycone moiety is amino-substituted are described for example in The Jornal of Antibiotics p. 1720–1730 November 93; Tetrahedron Vol. 37, No. 24, 4219–4228 (1981); DE 27 51 395; Carbohydrate Research, 228, 171–90 (1992) and DE-3641833. Compunds having three glycoside moieties and for which no activity data are reported, are described in WO 92/07862.

As known, however, the severe side effects caused by the anticancer agents used at present impose limits on the use of same in a good number of patients who, otherwise, would benefit from the treatment. Moreover, remarkable advances are needed in the treatment of some important solid tumours, e.g. pulmonary and ovarial, that do not adequately respond to any current treatment.

It follows that there is an urgent need for the coming onto the market of drugs highly selective in their inhibitory action against the proliferation of diseased cells compared with the normal ones.

DETAILED DESCRIPTION OF THE INVENTION

It is an object of the present invention to provide new anticancer compounds, in particular anthracycline analogues, in which the carbohydrate portion consists of a disaccharide residue.

It has surprisingly been found that the claimed anthracycline disaccharides, in which the sugar directly bound to aglycone never contains amino groups, exhibit higher anticancer activity and selectivity than the anthracycline previously known. It is worth noting that in the known anthracyclines, having similar structure and which contain two carbohydrate residues, the sugar bound to aglycone always contains a free or substituted amino group.

The compounds according to the present invention are the compounds of general formula (I) and (II), as reported above, and their pharmaceutically acceptable salts where R, $R_1$, $R_2$, $R_3$, $R_4$, and $R_5$ are as described above.

The present invention is also referred to pharmaceutical compositions containing said compounds, or salts thereof with pharmaceutically acceptable acids, preferably hydrochloric acid.

Particularly preferred are the following compounds:

a) 7-0-[2,6-dideoxy-4-0-(2,3,6-trideoxy-3-amino-α-L-lyxo-exopyranosyl)-α-L-lyxo-exopyranosyl] daunorubicinone chlorhydrate;

b) 7-0-[2,6-dideoxy-4-0-(2,3,6-trideoxy-3-amino-α-L-lyxo-exopyranosyl)-α-L-arabino-exopyranosyl] daunorubicinone chlorhydrate;

c) 7-0-[2,6-dideoxy-4-0-(2,3,6-trideoxy-3-amino-α-L-lyxo-exopyranosyl)-α-L-lyxo-exopyranosyl] doxorubicinone chlorhydrate;

d) 7-0-[2,6-dideoxy-4-0-(2,3,6-trideoxy-3-amino-α-L-lyxo-exopyranosyl)-α-L-arabino-exopyranosyl] doxorubicinone chlorhydrate;

e) 7-0-[2,6-dideoxy-4-0-(2,3,6-trideoxy-3-amino-α-L-lyxo-exopyranosyl)-α-L-arabino-exopyranosyl]-4-demethoxy-daunorubicinone chlorhydrate;

f) 7-0-[2,6-dideoxy-4-0-(2,3,6-trideoxy-3-amino-α-L-lyxo-exopyranosyl)-α-L-lyxo-exopyranosyl]-4-demethoxy-daunorubicinone chlorhyrate;

g) 7-0-[2,6-dideoxy-4-0-(2,3,6-trideoxy-3-amino-α-L-lyxo-exopyranosyl)-α-L-lyxo-exopyranosyl]-4-demethoxy-doxorubicinone chlorhydrate;

h) 7-0-[2,6-dideoxy-4-0-(2,3,6-trideoxy-3-amino-α-L-lyxo-exopyranosyl-α-L-arabino-exopyranosyl]-4-demethoxy-doxorubicinone chlorhydrate;

i) 7-0-[2,6-dideoxy-4-0-(2,3,4,6-tetradeoxy-4-amino-α-L-erythro-exopyranosyl)-α-L-lyxo-exopyranosyl] daunorubicinone chlorhydrate;

j) 7-0-[2,6-dideoxy-4-0-(2,3,4,6-tetradeoxy-4-amino-α-L-erythro-exopyranosyl)-α-L-lyxo-exopyranosyl]-4-demethoxy-daunorubicinone chlorhydrate;

k) 7-0-[2,6-dideoxy-4-0-(2,3,4,6-tetradeoxy-4-amino-α-L-erythro-exopyranosyl)-α-L-lyxo-exopyranosyl] doxorubicinone chlorhydrate;

l) 7-0-[2,6-dideoxy-4-0-(2,3,4,6-tetradeoxy-4-amino-α-L-erythro-exopyranosyl)-α-L-lyxo-exopyranosyl]-4-demethoxy-doxorubicinone chlorhydrate;

m) 7-0-[2,6-dideoxy-4-0-(2,3,6-trideoxy-3-amino-α-L-lyxo-exopyranosyl)-α-L-lyxo-exopyranosyl]-4-demethoxy-8-fluoro-daunorubicinone chlorhydrate;

n) 7-0-[2,6-dideoxy-4-0-(2,3,6-trideoxy-3-amino-α-L-lyxo-exopyranosyl)-α-L-lyxo-exopyranosyl]-4-demethoxy-8-fluoro-doxorubicinone chlorhydrate.

The compounds of general formula (I) and (II) can be prepared by a process consisting of the following steps:

a) condensation of a compound of formula (III)

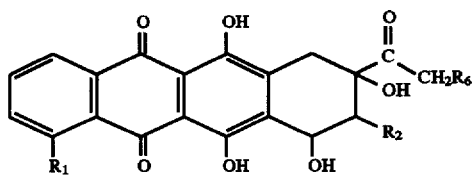

(III)

where $R_1$ and $R_2$ are as defined above and $R_6$ is H or the $OR_7$ group where $R_7$ is a protective group for an alcoholic function, preferably selected among the acetyl-, dimethylterbutylsilyl- or p-methoxyphenyldiphenylmethyl-groups, with a compound of formula (IV) or (V):

(IV)

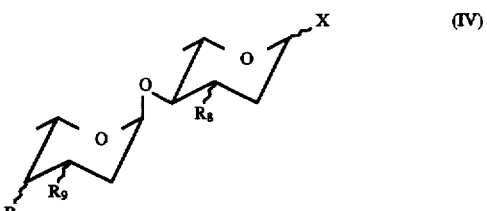

(V)

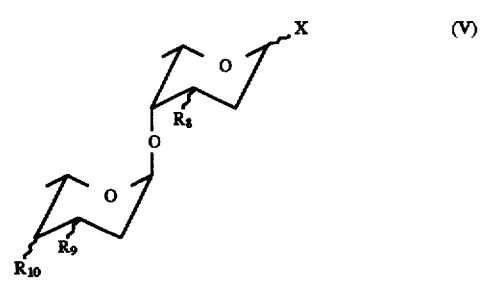

where $R_8$ is H or a protected —OH group, preferably p-nitrobenzoate; $R_9$ and $R_{10}$, identical or different, are each H or a protected OH group, preferably p-nitrobenzoate or a protected $NH_2$ group, preferably trifluoroacetamide or allyl-carboxyamide and X is a group capable of generating, under the condensation conditions, a stable carbo-cation that may bind itself to a hydroxyl group in position C-7 of the compound of formula (III), said group X being conveniently selected among the groups used in glycosidation reactions, e.g. a halogen such as chlorine or bromine, preferably chlorine, or a p-nitrobenzoyloxy group. Compounds of formula (VI) or (VII) are thus obtained:

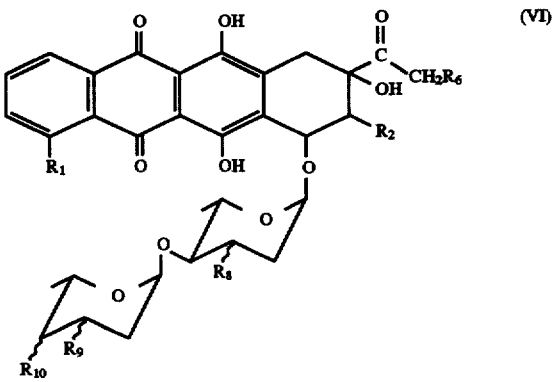

(VI)

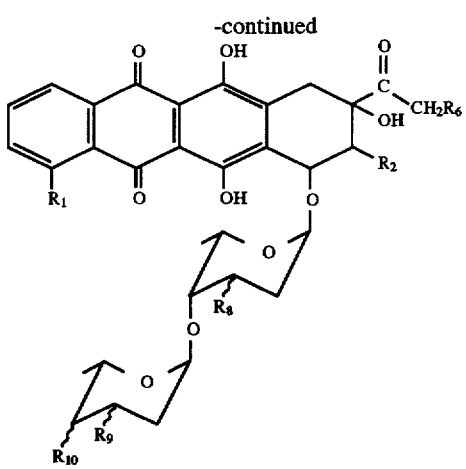

where $R_1$, $R_2$, $R_6$, $R_8$, $R_9$, $R_{10}$ and symbol ⁓ are as defined above;

b) one or more reaction/s of removal of the protective groups of OH and/or $NH_2$ functions from compounds of formula (VI) and (VII) to give compounds of formula (I) and (II), where R, $R_1$, $R_2$, $R_3$, $R_4$, $R_5$ and symbol ⁓ are as defined above;

c) conversion, if any, of the aforesaid glycosides of formula (I) and (II) into a pharmaceutically acceptable salt thereof, preferably chlorhydrate.

The reaction conditions for the glycosidation of a compound of formula (III) with a compound of formula (IV) or (V) to give a compound of formula (VI) or (VII) may vary depending on the type of substituents present in the compounds of formula (IV) or (V).

Glycosidation is carried out in an inert organic solvent in the presence of a condensing agent.

The condensing agents used are, e.g., silver trifluoromethane sulphonate, silver perchlorate, mixtures of mercury oxide and mercury bromide, boron halides, titanium or tin tetrachloride or ion exchange resins, such as Amberlite®, silver triflate, trimethylsilyltriflate, p-toluensulphonic acid, trifluoroacetic acid.

Glycosidation is preferably carried out with 1:1 to 1:3 molar ratios in an inert organic solvent, such as for example benzene, toluene, ethyl ether, tetrahydrofuran, dioxane; chloroform, methylene chloride or dichloroethane and mixtures thereof.

The reaction temperature may range from –40° C. 40° C., preferably from –20° C. to 20° C., and the reaction time from 15 min to 3 hrs.

The reaction mixture may include a dehydrating substance, such as an activated molecular sieve.

In the course of the reaction or at the reaction end, the reaction mixture may be added with an organic base, such as pyridine, collidine, N,N-dimethylaminopyridine, triethylamine or 1,8-bis-(dimethylamino)-naphthalene.

According to the present invention, the removal of the protective groups for OH and/or $NH_2$ functions from compounds of formula (VI) and (VII) to give compounds of formula (I) may be carried out under different conditions depending on the type of protective group used.

When $R_9$ and/or $R_{10}$, identical or different, are each a protected $NH_2$ group such as trifluoroacetamide or a protected OH group such as p-nitrobenzoate, and/or R is a protected OH group such as p-nitrobenzoate, and/or $R_6$ is a protected OH group such as acetate, deprotection reactions are carried out in a polar solvent, such as water, methanol, ethanol, pyridine, dimethylformamide or mixtures thereof and in the presence of an inorganic base, in a stoichiometric amount or in excess of the stoichiometric, such as sodium, potassium, lithium or barium hydroxide or carbonate.

The reaction temperature may range from 0° C. to 50° C. and the reaction time from 3 hrs to 48 hrs.

When $R_9$ and/or $R_{10}$ are each a protected $NH_2$ group such as allylcarboxyamide, deprotection is carried out in an inert solvent and in the presence of a metal complex such as tetrakis(triphenylphosphine)palladium, as disclosed, e.g., in Tetrahedron Letters, 30, 3773 (1989), or tetracarbonyl nickel, as disclosed, e.g., in J. Org. Chem., 38, 3233 (1973).

When $R_6$ is a protected OH group such as dimethylterbutylsilylether, deprotection is carried out in an inert solvent and in the presence of tetrabutylammonium fluoride, as disclosed, e.g. in J. of Antibiot., 37, 853 (1984).

When $R_6$ is a protected OH group such as p-methoxyphenyldiphenylmethylether, deprotection is carried out in an acid medium, e.g. in aqueous acetic acid, as disclosed, e.g. in J. Org. Chem., 42, 3653 (1977).

Compounds of formula (III) are either known or may be prepared according to methods and processes known in organic chemistry, as disclosed, e.g. in Gazz. Chim. Ital., 114, 517 (1984), in Bull. Chem. Soc. Jpn., 59, 423 (1986), and in the aforementioned Italian patent application by the Applicant, whose disclosures are incorporated herein by reference.

Compounds of formula (IV) or (V) are either known or may be prepared according to methods and processes for the synthesis of disaccharides known in organic chemistry [J. Carbohydr. Chem., 10, 833 (1991); Carbohydr. Res., 74, 199 (1979); Carbohydr. Res., 208, 111 (1980); Tetrahedron, 46, 103 (1990)].

Alternatively, if so desired, anthracycline glycosides of formula (I) and (II), where $R_1$, $R_2$, $R_3$, $R_4$, $R_5$ are as defined above and R is an OH group, may be prepared from glycosides of formula (I) and (II) or from pharmaceutically acceptable salts thereof, where $R_1$, $R_2$, $R_3$, $R_4$, $R_5$ and symbol ⁓ are as defined above and R is H, by bromination of the carbon in position 14 with bromine in chloroform followed by hydrolysis, at room temperature for a period of 48 hrs, of the resulting 14-bromoderivatives with sodium formate.

If so desired, glycosides of formula (I) and (II) may be converted into their pharmaceutically acceptable salts, e.g. chlorhydrates, by treatment with hydrochloric acid in methyl alcohol.

The present invention also relates to pharmaceutical compositions containing, as active ingredient, a compound of formula (I) or (II) or a pharmaceutically acceptable salt thereof combined with a pharmaceutically acceptable diluent or carrier.

According to the present invention, a therapeutically effective dose of a compound of formula (I) or (II) is combined with an inert carrier.

The compositions may be formulated in a conventional manner using common carriers.

The claimed compounds are useful for the therapeutic treatment on humans and other mammals. In particular, said compounds are good anticancer agents when administered in therapeutically effective doses.

The following examples illustrate the present invention in more detail.

EXAMPLE 1

7-O-[2,6-dideoxy-4-O- (2,3,6-trideoxy-3-amino-α-L-lyxo-exopyranosyl) -α-L- lyxo-exopyranosyl]-4- demethoxy-daunorubicinone chlorhydrate (compound of formula II, R=$R_1$=$R_2$=H, $R_3$=$R_5$=OH, $R_4$=$NH_2$).

A mixture of 4-demethoxydaunorubicinone (compound of formula III, $R_1$=$R_2$=$R_6$=H) (300 mg, 0.81 mmol) and 2,6-dideoxy-4-O-(2,3,6-trideoxy-4-O- p-nitrobenzoyl-3-trifluoroacetamido-α-L-lyxo-exopyranosyl)-3-O-p-nitrobenzoyl-α-L-lyxo-exopyranosyl-p-nitrobenzoate (compound of formula IV, $R_3$=$R_5$=p-nitrobenzoyl-oxy-, $R_4$=trifluoroacetamido-, X=p- nitrobenzoyloxy-) (600 mg, 0.72 mmol) in methyl chloride (72 ml) and ethyl ether (24 ml) in the presence of molecular sieves (A4) at −20° C. was treated with trimethylsilyltriflate (266 µl; 1.44 mmol). The reaction mixture was stirred for 1 hr. then it was diluted with methylene chloride, washed with a saturated sodium bicarbonate solution, and evaporated to dryness. The residue was separated by chromatography on silica gel (eluent $CH_2Cl_2$-EtOH, 99/1) yielding 360 mg of 7-0-[2,6- dideoxy-4-0-(2,3,6-trideoxy-4-0-p-nitrobenzoyl-3-fluoroacetamido-α-L-lyxo-exopyranosyl)-3-0-p-nitrobenzoyl-α-L-lyxo-exopyranosyl]-4- demethoxydaunorubicinone (compound of formula VII, $R_1$=$R_2$=$R_6$=H, $R_8$=$R_{10}$=p- nitrobenzoyloxy-, $R_9$=trifluoroacetamido-).

A protected diglycoside suspension of compound of formula (VII) ($R_1$=$R_2$=$R_6$=H, $R_8$=$R_{10}$=p-nitrobenzoyloxy-, $R_9$=trifluoroacetamido-) (120 mg; 0.117 mmol) in 17.6 ml of a 0.1M solution of $Ba(OH)_2$ in $H_2O$/MeOH, 1/1, was maintained under stirring at room temperature for a period of 3 hrs. The reaction mixture was neutralized with a 0.2M potassium bisulphate solution and extracted with chloroform; the organic extracts were collected together, dried over anhydrous sodium sulphate, evaporated to dryness, and taken up with 0.002M HCl solution. The acid aqueous solution was washed with chloroform and freeze-dried to give 62 mg of the desired product (compound of formula II, (R=$R_1$=$R_2$=H, $R_3$=$R_5$=OH, $R_4$=$NH_2$). Yield 39%.

The NMR data obtained are reported below:

$^1$H-NMR (DMSO-$d_6$), δ 1.05 (d,3H), 1.15 (d,3H), 1.5–1.95 (m,4H), 2.1 (m,2H), 2.25 (s,3H), 2.95 (dd, 2H), 3.55 (s,2H), 3.8 (m,1H), 3.95 (m,1H), 4.15 (q,1H), 4.35 (q,1H), 4.6 (d,1H), 4.9 (bs,2H), 5.25 (bs,1H), 5.35 (d,1H), 5.55 (s,1H), 7.95 (bs,2H), 8.25 (bs,2H).

According to an analogous process, also the following compounds of formula (I) and (II) were obtained:

7-0-[2,6-dideoxy-4-0-(2,3,6-trideoxy-3-amino-α-L-lyxo-exopyranosyl)-α-L-lyxo-exopyranosyl] daunorubicinone chlorhydrate (compound of formula II, R=$R_2$=H, $R_1$=OCH$_3$, $R_3$=$R_5$=OH, $R_4$=$NH_2$).

$^1$H-NMR (DMSO-$d_6$), δ 1.05 (d,3H), 1.15 (d,3H), 1.35–2.15 (m,6H), 2.25 (s,3H), 2.95 (dd,2H), 3.55 (bs,2H), 3.8 (m,1H), 3.95 (s,3H), 4.05–4.2 (m+q,2H), 4.35 (q,1H), 4.9 (bs,2H), 5.25 (d,1H), 7.65 (m,1H), 7.9 (d,2H).

7-0-[2,6-dideoxy-4-0-(2,3,6-trideoxy-3-amino-α-L-lyxo-exopyranosyl)-α-L-arabino-exopyranosyl] daunorubicinone chlorhydrate (compound of formula I; R=$R_2$=H, $R_1$=OCH$_3$, $R_3$=$R_5$=OH, $R_4$=$NH_2$).

$^1$H-NMR (DMSO-$d_6$), δ 1.13 (d,3H), 1.15 (d,3H), 1.45–1.85 (m,4H), 2.05 (m,2H), 2.15 (s,3H), 2.87 (dd, 2H), 2.98 (m,1H), 3.5 (m,1H), 3.6 (m,1H), 3.85 (q,1H), 3.9 (q,1H), 3.9 (s,3H), 4.84 (m,2H), 5.13 (bs,1H), 5.28 (s,1H), 5.32 (d,1H), 5.55 (s,1H), 7.55 (m, 1H), 7.8 (m,2H).

7-0-[2,6-dideoxy-4-0-(2,3,6-trideoxy-3-amino-α-L-lyxo-exopyranosyl)-α-L-arabino-exopyranosyl]-4-demethoxy-daunorubicinone chlorhydrate (compound of formula I; R=$R_1$=$R_2$=H, $R_3$=$R_5$=OH, $R_4$=$NH_2$).

$^1$H-NMR (DMSO-$d_6$), δ 1.1 (d,3H), 1.2 (d,3H), 1.5–1.95 (m,4H), 2.05–2.2 (m,2H), 2.25 (s,3H), 2.95 (dd,2H), 3.1 (t,1H), 3.4 (m,1H), 3.6 (bs,1H), 3.65 (m,1H), 3.85–4.00 (q+q,2H), 3.9 (m,1H), 4.95 (d,1H), 5.2 (d,1H), 5.4 (bs,2H), 5.7 (s,1H), 7.95 (m,2H), 8.25 (m, 2H).

TABLE 1

Cytotoxic Activity (in vitro)

| Cell line | Drug exposure (h) | IC$_{50}$ (ng/ml) | | | |
|---|---|---|---|---|---|
| | | DXR | IIa | IIb | IIc |
| LOVO (colon) | 24 | 10 | 6.5 | 8.5 | 10 |
| MCF-7 (breast) | " | 10 | 10 | 15 | 5.6 |
| A431 (cervix) | " | 36 | 12 | 26 | 16 |
| A2780 (ovarian) | " | 30 | 1 | 10 | 5 |
| H-460 (non-small cell lung cancer) | " | 20 | 15 | 18 | 10 |
| POVD (small cell lung cancer) | 96 | 34 | 15 | 20 | 11 |

TABLE 2

Effect against human ovarian carcinoma A2780 (in vivo)

| Compound | optimal dose mg/Kg | day of treatment | tumor inhibition % | toxicity deaths |
|---|---|---|---|---|
| DXR | 7 | 11, 18, 25 | 68 | 0/5 |
| II$_a$ | 8.5 | 11, 18, 25 | 75 | 0/5 |
| II$_c$ | 5 | 11, 15, 18, 21, 25 | 99 | 0/5 |

TABLE 3

Effect against human small cell lung carcinoma POVD (in vivo)

| Compound | optimal dose mg/Kg | day of treatment | tumor inhibition % | toxicity deaths |
|---|---|---|---|---|
| DXR | 7 | 10, 17, 24 | 44 | 0/5 |
| II$_a$ | 8.5 | 10, 17, 24 | 80 | 0/5 |
| II$_c$ | 5 | 10, 14, 17, 21, 24 | 91 | 0/5 |

Biological Activity

IIa: 7-0-[2,6-dideoxy-4-0-(2,3,6-trideoxy-3-amino-a-L-lyxo-exopyranosyl)-a-L-lyxo- exopyranosyl]-4-demethoxy-daunorubicinone hydrochloride (II, R=H, $R_1$=H, $R_{3eq}$=$R_{5ax}$=OH, $R_{4eq}$=$NH_2$);

II$_b$: 7-0-[2,6-dideoxy-4-0-(2,6-dideoxy-a-L-lyxo-exopyranosyl)-a-L-lyxo- exopyranosyl]-4-demethoxy-doxorubicinone hydrochloride (II, R=OH, $R_1$=H, $R_{3eq}$=$R_{5ax}$=OH, $R_{4eq}$=OH);

II$_c$: 7-0-[2,6-dideoxy-4-0-(2,3,6-trideoxy-3amino-a-L-lyxo-exopyranosyl)-a-L-lyxo- exopyranosyl]-4-demethoxy-doxorubicinone hydrochloride (II, R=OH, $R_1$=H, $R_{3eq}$=$R_{5ax}$=OH, $R_{4eq}$=$NH_2$);

was tested, in comparison with doxorubicin, against a variety of human tumors of different histotypes including ovarian carcinoma, lung cancer , breast cancer, cervical carcinoma, colon cancer.

In Vitro Activity

Cell survival, following test compound exposure, was evaluated by the growth inhibition test, with the exception of small cell lung cancer cell lines (SCLC). Cells in the logarithmic phase of growth were harvested and placed into 6-well. Twenty-four h after seeding, cells were exposed to test compounds for different times. After replacement with drug-free medium, cells were harvested and counted 72 h following compound exposure. In the case of SCLC, MCF-7 and LOVO, the MTT assay has been used and the colorimetric evaluation of survival was performed at the end of the incubation time (24 or 96 h). The results obtained from cytotoxicity experiments are expressed as $IC_{50}$ (i.e., concentration required for 50% inhibition of cell growth).

The test compounds were dissolved in distilled water and then diluted in culture medium.

The results are reported in Table 1.

The compounds of the invention IIa–IIc show remarkable cytotoxic effects with a potency comparable or higher as compared to DXR.

In Vivo Studies

For in vivo studies athymic mice were injected subcutaneous with tumor fragments in both flanks. Growth of tumors was followed by twice weekly caliper measurement of length and width. Tumor weight was calculated using the formula: mg=volume in $mm^3$=$width^2 \times length/2$ (considering density=1).

The test compounds were delivered, at the optimal doses and schedules, intravenously (i.v.) to tumor-bearing mice starting at different times in the different tumors using (see experiments for details). The effects achieved by the treatments were expressed as Tumor Weight Inhibition % (TWI%) in treated versus control mice, determined 7–10 days after the last drug treatment. The results are reported in tables 2 and 3.

Against A2780 ovarian carcinoma, compound $II_a$ shows at least the same effectiveness than doxorubicin, whereas compound $II_c$ achieves an antitumor activity greatly superior to that of the parent compund, reducing the the tumor growth by 99%.

On SCLC tumor POVD refractory to DXR (doxorubicin) treatment, both compounds $II_a$ and $II_c$ exhibit a very high antitumor activity.

We claim:

1. A compound of formula (I) or (II), respectively

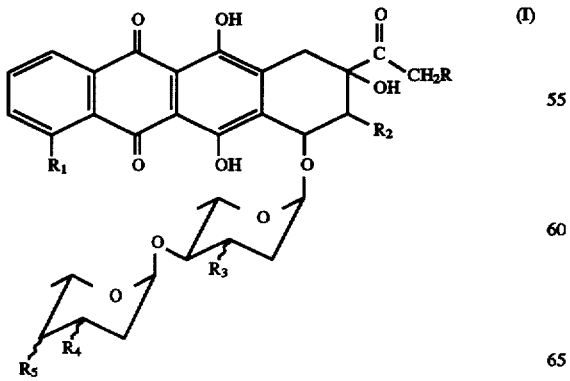

(I)

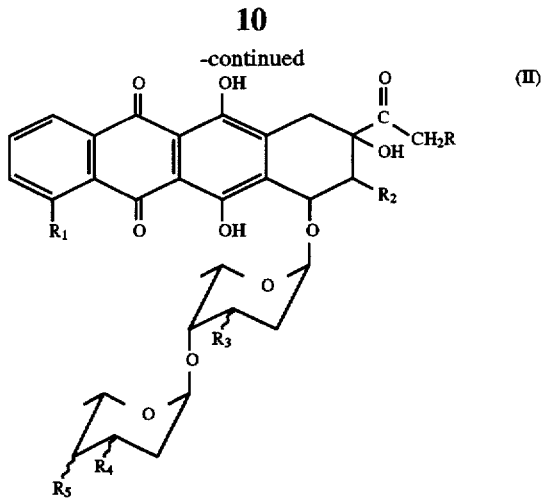

(II)

where:

R is H or OH or the $OR_7$ group where $R_7$=CHO or $COCH_3$ or the acylic residue of a carboxylic acid containing up to 6 carbon atoms;

$R_1$ is H or OH or $OCH_3$;

$R_2$ is H or F;

$R_3$ is H or OH;

$R_4$ and $R_5$, identical or different, are each H or OH or $NH_2$;

and bond symbol ⸺ indicates that substituents $R_3$, $R_4$, and $R_5$ may be in an axial or equatorial position, or its pharmaceutically acceptable salt.

2. Compounds of formula (I) or (II) according to claim 1 selected from the group consisting of:

a) 7-0-[2,6-dideoxy-4-0-(2,3,6-trideoxy-3-amino-α-L-lyxo-exopyranosyl)-α- L-lyxo-exopyranosyl] daunorubicinone chlorhydrate;

b) 7-0-[2,6-dideoxy-4-0-(2,3,6-trideoxy-3-amino-α-L-lyxo-exopyranosyl)-α- L-arabino-exopyranosyl] daunorubicinone chlorhydrate;

c) 7-0-[2,6-dideoxy-4-0-(2,3,6-trideoxy-3-amino-α-L-lyxo-exopyranosyl)-α- L-lyxo-exopyranosyl] doxorubicinone chlorhydrate;

d) 7-0-[2,6-dideoxy-4-0-(2,3,6-trideoxy-3-amino-α-L-lyxo-exopyranosyl)-α- L-arabino-exopyranosyl] doxorubicinone chlorhydrate;

e) 7-0-[2,6-dideoxy-4-0-(2,3,6-trideoxy-3-amino-α-L-lyxo-exopyranosyl)-α- L-arabino-exopyranosyl]-4-demethoxy-daunorubicinone chlorhydrate;

f) 7-0-[2,6-dideoxy-4-0-(2,3,6-trideoxy-3-amino-α-L-lyxo-exopyranosyl)-α- L-lyxo-exopyranosyl]-4-demethoxy-daunorubicinone chlorhyrate;

g) 7-0-[2,6-dideoxy-4-0-(2,3,6-trideoxy-3-amino-α-L-lyxo-exopyranosyl)-α- L-lyxo-exopyranosyl]-4-demethoxy-doxorubicinone chlorhydrate;

h) 7-0-[2,6-dideoxy-4-0-(2,3,6-trideoxy-3-amino-α-L-lyxo-exopyranosyl)-α- L-arabino-exopyranosyl]-4-demethoxy-doxorubicinone chlorhydrate;

i) 7-0-[2,6-dideoxy-4-0-(2,3,4,6-tetradeoxy-4-amino-α-L-erythro- exopyranosyl)-α-L-lyxo-exopyranosyl] daunorubicinone chlorhydrate;

j) 7-0-[2,6-dideoxy-4-0-(2,3,4,6-tetradeoxy-4-amino-α-L-erythro- exopyranosyl)-α-L-lyxo-exopyranosyl]-4-demethoxy-daunorubicinone chlorhydrate;

k) 7-0-[2,6-dideoxy-4-0-(2,3,4,6-tetradeoxy-4-amino-α-L-erythro- exopyranosyl)-α-L-lyxo-exopyranosyl] doxorubicinone chlorhydrate;

l) 7-0-[2,6-dideoxy-4-0-(2,3,4,6-tetradeoxy-4-amino-α-L-erythro- exopyranosyl)-α-L-lyxo-exopyranosyl]-4-demethoxy-doxorubicinone chlorhydrate;

m) 7-0-[2,6-dideoxy-4-0-(2,3,6-trideoxy-3-amino-α-L-lyxo-exopyranosyl)-α- L-lyxo-exopyranosyl]-4-demethoxy-8-fluoro-daunorubicinone chlorhydrate; and n) 7-0-[2,6-dideoxy-4-0-(2,3,6-trideoxy-3-amino-α-L-lyxo-exopyranosyl)-α- L-lyxo-exopyranosyl]-4-demethoxy-8-fluoro-doxorubicinone chlorhydrate.

3. Process for the preparation of a compound of formula (I) or (II), respectively

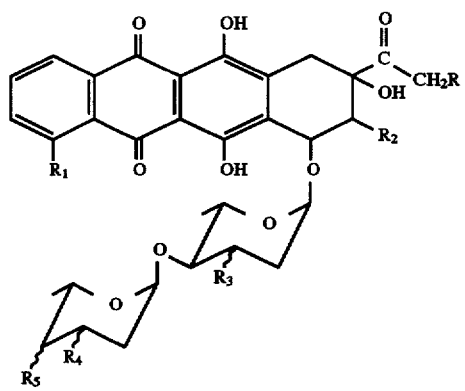

(I)

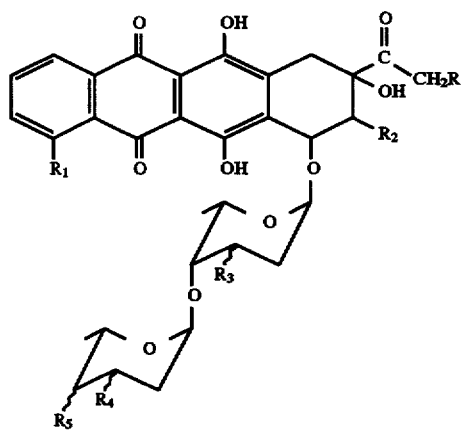

(II)

where:

R is H or OH or the $OR_7$ group where $R_7$ [=] is selected from the group consisting of CHO, $COCH_3$ and the acylic residue of a carboxylic acid containing up to 6 carbon atoms;

$R_1$ is H or OH or $OCH_3$;

$R_2$ is H or F;

$R_3$ is H or OH;

$R_4$ and $R_5$, identical or different, are each H or OH or $NH_2$;

and bond symbol --- indicates that substituents $R_3$, $R_4$, and $R_5$ may be either in axial or equatorial position, or their pharmaceutically acceptable salts consisting of the following steps:

i) condensation of a compound of formula (III)

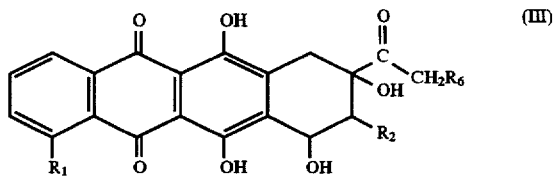

(III)

where $R_1$ and $R_2$ are as defined above and $R_6$ is H or the $OR_7$ group where $R_7$ is a protective group for an alcoholic function, selected from the group consisting of acetyl-, dimethylterbutylsilyl- and p-methoxyphenyldiphenylmethyl- groups, with a compound of formula (IV) or (V):

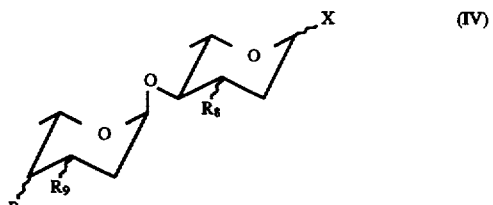

(IV)

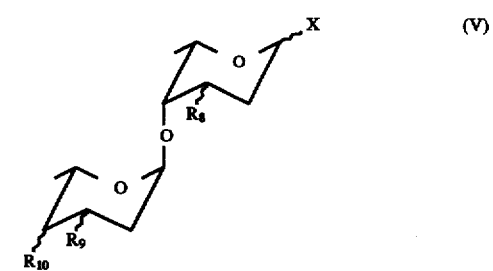

(V)

where $R_8$ is H or a protected —OH group; $R_9$ and $R_{10}$, identical or different, are each H or a protected OH group or a protected $NH_2$ group, and X is selected from the group consisting of halogen and p-nitrobenzoyloxy, to give compounds of formula (VI) or (VII):

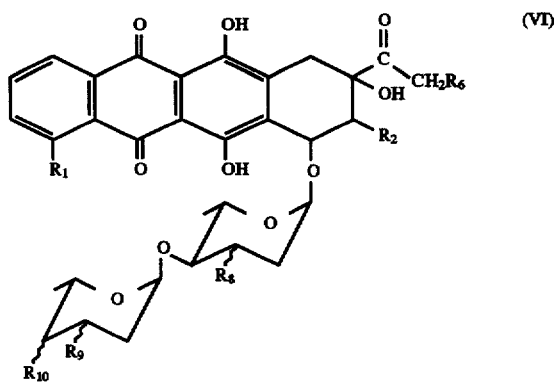

(VI)

-continued

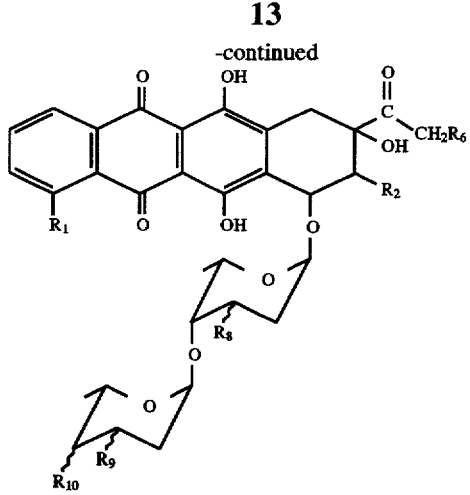

(VII)

where $R_1$, $R_2$, $R_6$, $R_8$, $R_9$, $R_{10}$ and symbol ⁓ are as defined above;

ii) one or more reaction/s of removal of the protective groups for OH and/or $NH_2$ functions from compounds of formula (VI) and (VII) to give compounds of formula (I) and (II), where R, $R_1$, $R_2$, $R_3$, $R_4$, $R_5$ and symbol ⁓ are as defined above;

iii) conversion, of the compounds of formula (I) and (II) into a pharmaceutically acceptable salt thereof.

4. Process for the preparation of the compounds of formula (I) and (II) according to claim 1, wherein $R_1$, $R_2$, $R_3$, $R_4$, $R_5$ are as defined in claim 1 and R is an OH group, or their pharmaceutically acceptable salts, consisting of the following steps:

i) bromination of the carbon in position 14 of the compounds of formula (I) and (II) or of their pharmaceutically acceptable salts, where $R_1$, $R_2$, $R_3$, $R_4$, $R_5$ and symbol ⁓ are as defined above and R is H;

ii) hydrolysis of the resulting 14-bromoderivatives to obtain compounds of formula (I) and (II), where $R_1$, $R_2$, $R_3$, $R_4$, $R_5$ are as defined above and R is the OH group.

5. The process according to claim 3 wherein in the compound of formula (IV) or (V) according to claim 3 $R_8$ is H or a protected OH group $R_9$ and $R_{10}$, identical or different, are each H or a protected OH group selected from the group consisting of p-nitrobenzoyl-, or an $NH_2$ protected by a trifluoroacetyl- or a allyloxycarbonyl-group.

6. The process according to claim 3 wherein phase i) is carried out in the presence of a condensing agent selected from the group consisting of silver triflate, silver perchlorate, mixtures of mercury oxide and mercury bromide, trimethylsilyltriflate, p-toluenesulphonic acid, trifluoroacetic acid, boron halides, tin tetrachloride, titanium tetrachloride and ion exchange resins.

7. The process according to claim 3 wherein the compound of formula (III) is dissolved in an inert organic solvent and the condensation is carried out in the presence of molecular sieves as dehydrating substances.

8. The process according to claim 6 wherein the reaction mixture is added during condensation with an organic base selected from the group consisting of pyridine, collidine, N,N-dimethylaminopyridine, triethylamine and 1,8-bis-(dimethylamino)-naphthalene.

9. The process according to claim 3 wherein said halogen in phase i) is chlorine or bromine.

10. The process according to claim 3 wherein in phase ii) a trifluoroacetyl group, which protects a $NH_2$ function, and/or p-nitrobenzoyl- and/or acetyl- groups, which protect OH functions, are removed by the action of an inorganic base selected from the group consisting of hydroxides and cabonates sodium, potassium, lithium and barium.

11. The process according to claim 3 wherein in phase ii) an allyloxycarbonyl group, which protects a NH2 function, is removed by the action of nickel or palladium organic complexes.

12. The process according to claim 3 wherein in phase ii) a methoxyphenyldiphenylmethyl group, which protects an OH function, is removed by the action of an organic acid.

13. The process according to claim 12 wherein the said organic acid is acetic acid.

14. The process according to claim 3 wherein in phase ii) the dimethylterbutylsilyl group, which protects an OH function, is removed in the presence of tetrabutylammonium fluoride.

15. The process according to claim 3 wherein in phase iii) the compounds of formula (I) and (II) are converted into pharmaceutically acceptable chlorhydrates.

16. The process according to claim 4 wherein in phase i) bromination is carried out with bromine in chloroform.

17. The process according to claim 4 wherein in phase ii) hydrolysis is carried out with sodium formate.

18. A pharmaceutical composition containing as active ingredient at least one compound according to claim 1 or a pharmaceutically acceptable salt thereof, combined with a pharmaceutically acceptable carrier or diluent.

* * * * *